United States Patent [19]

Klotzsch et al.

[11] Patent Number: 4,543,337
[45] Date of Patent: Sep. 24, 1985

[54] STABILIZER FOR UREA NITROGEN COLOR REAGENT

[75] Inventors: Sigrid G. Klotzsch, Irvington; Richard Vadaszy, Valley Cottage, both of N.Y.

[73] Assignee: Technicon Instruments Corporation, Tarrytown, N.Y.

[21] Appl. No.: 595,145

[22] Filed: Mar. 30, 1984

[51] Int. Cl.$^4$ ............................................. G01N 33/62
[52] U.S. Cl. ..................................... 436/108; 252/402
[58] Field of Search ................ 436/108, 176; 252/397, 252/402, 188.2

[56] References Cited

U.S. PATENT DOCUMENTS

| | | | |
|---|---|---|---|
| 3,890,099 | 6/1975 | Jung | 436/108 |
| 4,273,556 | 6/1981 | Gindler | 436/108 |
| 4,357,144 | 11/1982 | Gindler | 436/108 |

OTHER PUBLICATIONS

Fearon, Biochem. J., vol. 33, pp. 902–907, (1939).
Koritz et al., J. Bio. Chem., vol. 209, pp. 145–150, (1954).
Ormsby, J. Biol. Chem., vol. 146, pp. 595–604, (1942).
Natelson et al., Am. J. Clin. Pathol., vol. 21, pp. 275–281, (1951).
Coulombe et al., Clin. Chem., vol. 9, pp. 102–108, (1963).
Pellerin, Clin. Chem., vol. 10, pp. 374–375, (1964).
Marsh et al., Clin. Chem., vol. 11, pp. 624–627, (1965).

*Primary Examiner*—Barry S. Richman
*Assistant Examiner*—Michael S. Gzybowski
*Attorney, Agent, or Firm*—Morgan, Finnegan, Pine, Foley & Lee

[57] ABSTRACT

A storage stable diagnostic reagent for colorimetric determination of urea nitrogen, the reagent having enhanced sensitivity, and comprises a chromogenic agent, a color enhancer, and a cyothioamine, as well as method employing said reagent.

8 Claims, No Drawings

STABILIZER FOR UREA NITROGEN COLOR REAGENT

BACKGROUND OF THE INVENTION

This invention relates generally to urea assay methodology and, more particularly, to a colorimetric urea nitrogen reagent and method employing same.

Essentially three groups of methods have been used for the determination of urea nitrogen (UN). They can be classified as miscellaneous methods, methods based on the reaction with diacetyl-monoxime or similar compounds, and methods employing urease. Methods employing diacetyl-monoxime and urease have become the most popular.

In 1939, Fearon [Biochem. J. 33:902–907 (1930)] found that the reaction of diacetyl monoxime (DAM) followed by oxidation produces colors with $R_1$ NH—CO—NHR$_2$ when $R_1$ is either H or a single aliphatic radical. $R_2$ is not an acyl radical and is usually hydrogen. Colors were produced with urea, creatinine, methylurea (and urea derivatives), allantoin, and proteins. Many urea substitutes yield a red pigment, but only urea produces a yellow color. [Koritz et al, J. Bio. Chem. 209:145–150 (1954)].

In 1942, Ormbsy [J. Biol. Chem. 146:595–604 (1942)] applied the diacetyl-monoxime (DAM) reaction in a strongly acidic medium to the determination of urea. The resultant color was intensified by oxidation with potassium persulfate. Other oxidants have been used and are also described in the literature.

Natelson, Scott and Beffa [Am. J. Clin. Pathol. 21:275–281 (1951)] obviated the need for oxidizing agents by use of free diacetyl rather than the derivative.

In 1963, Coulombe and Favreau [Clin. Chem. 9:102–108 (1963)] demonstrated the effect of thiosemicarbazide upon the direct reaction between diacetyl-monoxime and urea. This compound further intensified the color and inhibits photosensitivity. Subsequently, the semi-carbazide reagent was incorporated in the automated procedure described by Pellerin [Clin. Chem. 10:374–375 (1964)].

In 1965, Marsh, Fingerhut, and Miller [Clin. Chem. 11:624–627 (1965)] presented both an automated and a manual diacetyl-monoxime method for direct determination of urea. Both methods proved highly sensitive due to the combined use of thiosemicarbazide and ferric ions.

In spite of the above advances, such urea determinations have been plagued by instability of working solutions resulting in limited shelf life and potentially erroneous results.

SUMMARY OF THE INVENTION

The present invention provides for a storage stable diagnostic reagent useful for the colorimetric determination characterized by enhanced sensitivity and linearity, employed in a urea nitrogen method giving rapid and precise results.

It is an object of the invention to overcome the instability problems found in the prior art BUN color reagents and to provide a reagent having enhanced sensitivity and linearity.

Accordingly, to the present invention, a storage stable diagnostic reagent useful for the colorimetric determination of urea nitrogen characterized by enhanced sensitivity and linearity is disclosed and claimed which comprises:

(a) from about 0.02% to about 5.0% weight volume (w/v) of a chromogenic agent;

(b) from about 0.001% to about 0.2% w/v of a color enhancer; and (c) up to about 0.5% w/v of a cyanothioamine of the formula:

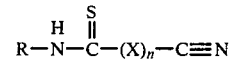

wherein R is alkyl; amino, mono- or dialkylamino, said alkyl having from 1 to 4 carbons; X is amino; n is 0, 1 or 2; and the thio salts thereof.

In a preferred embodiment, the chromogenic agent above is diacetyl monoxime or a derivative thereof.

In another preferred embodiment, the color enhancer is thiosemicarbazide.

In another preferred embodiment, the cyanothioamine is a compound having the formulae

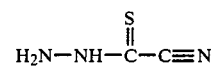

or

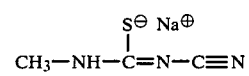

In another embodiment, the aforesaid reagents are used in a colorimetric determination of urea nitrogen in a urea-containing sample whereby the urea concentration of the sample is linearly related to a colored reaction product colorimetrically determinable at 520 nm.

DETAILED DESCRIPTION OF THE INVENTION

As described earlier, Coulombe and Favreau demonstrated the effect of thiosemicarbazide upon the direct reaction between diacetyl monoxime and urea, namely intensified color.

The present invention is directed to overcoming the instability found to exist in urea nitrogen color reagents comprising diacetyl monoxime and thiosemicarbazide.

There is a need to provide a reagent which is storage stable, i.e., stable for at least 6 months at room temperature and has fully sensitivity and linearity.

As used herein, "sensitivity" is defined as about 0.0022 absorbance units per mg. urea nitrogen/dl and "linearity" is defined as linear response to test samples in the range of 0–150 mg. urea nitrogen/dl.

The present invention provides a reagent which satisfies those needs.

According to the present invention, there is disclosed and claimed a novel reagent for colorimetrically assaying the urea content of fluids such as blood serum, plasma, urine and spinal fluid comprising:

(a) from about 0.02% to about 5.0% w/v of a chromogenic agent;

(b) from about 0.001% to about 0.2% w/v of a color enhancer; and (c) up to about 0.5% w/v of a cyanothioamine of the formula:

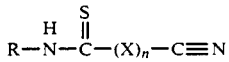

wherein R is alkyl; amino, mono- or dialkylamino, said alkyl having from 1 to 4 carbons; X is amino; n is 0, 1 or 2; and the thio salts thereof.

The chromogenic agent for use herein is preferably diacetyl, however, any derivative thereof, e.g., diacetyl monoxime may be used so long as the required ureide-group reaction takes place to provide a measurable yellow color.

It is further preferred to have from about 0.02% to about 5.0% w/v of said chromogenic agent in the reagent with from about 0.1% to about 0.3% w/v most preferred.

The color enhancer for use herein is preferably thiosemicarbazide, however, any material can be used which intensifies the aforedescribed color and change of hue from yellow to red.

It is preferred to have from about 0.001% w/v to about 0.2% w/v of said color enhancer and most preferred is a range from about 0.002% to about 0.5% w/v.

The cyanothioamine component as used herein can by any compound of the formula

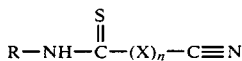

wherein R is alkyl; amino, mono- or dialkylamino, said alkyl having from 1 to 4 carbons; X is amino; n is 0, 1 or 2; and the thio salts thereof.

Preferred examples are the compounds

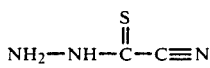

and

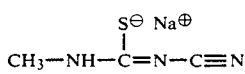

It is preferred to have up to about 0.5% w/v of said cyanothioamine compound in the reagent composition with the most preferred having a range of from about 0.02% to about 0.1% w/v.

It is also an object of this invention to provide a colorimetric assay for determining the urea content of fluids employing the diagnostic reagent described hereinabove.

Urea is the chief end product of protein metabolism in the blood, and its concentration in the blood provides an indicator of kidney function. The quantitative testing for urea is therefore an invaluable tool in the analysis of kidney malfunction.

Although the most preferred application of the method of this invention is to blood serum, it is to be understood that the method employing the herein disclosed and claimed diagnostic reagent is applicable to other body fluids as well such as blood plasma, urine, spinal fluid or any aqueous solution containing urea.

EXAMPLE I

This example describes the use of a composition of the invention in determining blood urea nitrogen on a SMAC analytical system. The SMAC system was used in this example in accordance with the written instructions available from the manufacturer, Technicon Instruments Corporation, Tarrytown, N.Y. 10591.

| Composition of Reagents: | | |
|---|---|---|
| A. | BUN Sample Diluent | |
| | deionized water | 1.0 l |
| | surfactant (a suitable surfactant is a 30% aq. solution of Brij.-35, a trademark of ICI Americas, Inc., Wilmington, Delaware) | 0.001 l |
| B. | BUN Color Reagent | |
| | deionized water | 1.0 l |
| | diacetyl monoxime | 2.0 g |
| | thiosemicarbazide | 0.2 g |
| | 1-cyano-3-methylisothiourea, sodium salt | 0.6 g |
| | surfactant and other non-active ingredients | |
| C. | BUN Acid Reagent | |
| | sulfuric acid, conc. | 0.25 l |
| | phosphoric acid, conc. | 0.0012 l |
| | ferric chloride, hexahydrate | 0.06 g |
| | deionized water | qs to 1 l |

A serum sample is introduced into the system and diluted in an air-segmented stream of BUN sample diluent to a ratio of 74 μl sample/287 μl diluent. After mixing, the diluted sample is exposed to a dialysis membrane. The urea dialyzes across the membrane into 385 μl of a steady stream of BUN color reagent. The analyte-containing BUN color reagent stream is then acidified with 226 μl BUN acid reagent. After acidifying by addition of BUN acid reagent, the stream of reaction mixture is heated to 90° C. at which point, the thiosemicarbazide intensifies the color. The absorbance of the reaction mixture stream is measured at 520 nm in a flowcell. The observed absorbance is proportional to the urea nitrogen in the sample and the urea nitrogen concentration is calculated by comparison with an appropriate standard.

It should be understood by those skilled in the art that various modifications may be made in the present invention without departing from the spirit and scope thereof as described in the specification and defined in the appended claims.

What is claimed is:

1. A storage stable diagnostic reagent solution useful for the colorimetric determination of urea nitrogen in a urea-containing sample characterized by enhanced sensitivity and linearity which comprises
   (a) from about 0.02% to about 5.0% w/v of a chromogenic agent;
   (b) from about 0.001% to about 0.2% w/v of a color enhancer; and
   (c) an effective amount of up to about 0.5% w/v of a cyanothioamine of the formula:

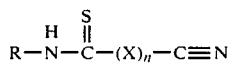

wherein R is alkyl; amino, mono- or dialkylamino, said alkyl having from 1 to 4 carbons; X is amino; n is 0, 1 or 2; and the thio salts thereof.

2. The reagent of claim 1 wherein said chromogenic agent is diacetyl monoxime or derivatives thereof.

3. The reagent of claim 1 wherein said color enhancer is thiosemicarbazide.

4. The reagent of claim 1 wherein said cyanothioamine is a compound of the formula:

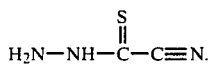

5. The reagent of claim 1 wherein said cyanothioamine is a compound of the formula:

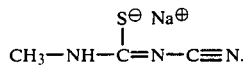

6. The reagent of claim 1 wherein said chromogenic agent is diacetyl monoxime, said color enhancer is thiosemicarbazide and said cyanothioamine is

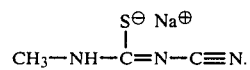

7. A colorimetric method for the determination of urea nitrogen in a urea-containing sample which comprises contacting the diagnostic reagent of claim 1 with a sample and observing any resultant change in color.

8. A colorimetric method for the determination of urea nitrogen in a urea-containing sample which comprises contacting the diagnostic reagent of claim 6 with a sample and observing any resultant change in color.

* * * * *